United States Patent [19]

Sutter et al.

[11] Patent Number: 5,667,384
[45] Date of Patent: Sep. 16, 1997

[54] DEVICE FOR FORMING A DENTAL PROSTHESIS AND METHOD OF MANUFACTURING SUCH A DEVICE

[75] Inventors: Franz Sutter, Niederdorf; Vincenzo Grande, Möhlin; Francis J. Sutter, Hölstein, all of Switzerland

[73] Assignee: Institut Straumann AG, Waldenburg, Switzerland

[21] Appl. No.: 442,944

[22] Filed: May 17, 1995

[30] Foreign Application Priority Data

Jun. 3, 1994 [CH] Switzerland .............. 1746/94

[51] Int. Cl.⁶ ...................................... A61C 8/00
[52] U.S. Cl. ........................... 433/172; 433/173
[58] Field of Search .................... 433/172, 213, 433/173

[56] References Cited

U.S. PATENT DOCUMENTS

| | | |
|---|---|---|
| 4,044,467 | 8/1977 | Linkow et al. . |
| 4,396,054 | 8/1983 | Cole ........................ 433/213 |
| 5,116,225 | 5/1992 | Riera ........................ 433/173 |
| 5,221,204 | 6/1993 | Kruger et al. ............. 433/172 |
| 5,234,339 | 8/1993 | Grigereit .................. 433/172 |
| 5,421,722 | 6/1995 | Stemmann ............... 433/172 |
| 5,429,505 | 7/1995 | Fortin ...................... 433/172 |
| 5,431,695 | 7/1995 | Wiklund et al. ......... 607/36 |
| 5,439,380 | 8/1995 | Marlin .................... 433/172 |

FOREIGN PATENT DOCUMENTS

| | | |
|---|---|---|
| 2029346 | 1/1969 | France . |
| 2429587 | 6/1978 | France . |

*Primary Examiner*—Cary E. O'Connor
*Attorney, Agent, or Firm*—Anderson Kill & Olick L.C.

[57] ABSTRACT

The device (1) for forming a dental prosthesis has at least one support (3) with a base (4) which in the use of the device (1) is inserted into a jawbone (13) of a patient or into a jaw model. The support (3) has a conical bearing surface (4n) and also a shoulder (7e) which faces the base (4) and for example is formed by a flank of an annular groove (7d). The device (1) has for the or each support (3) a cap (8) which bears with a conical countersurface (8f) on the conical bearing surface (4n) of the support (44) when the device (1) has been assembled. The cap (8) has a hole (8k) with an internal thread (8m) and with an axis (11) which forms an angle with the axis (10) of the two conical surfaces (4n, 8f). A screw (9) screwed into the hole (8k) engages with a tapering end section (9b) on the outer border (7f) of the shoulder (7e) and thus presses the countersurface (8f) against the bearing surface (4n). The end section (8b) of the cap (8) facing away from the base (4) is hole-free and therefore makes possible favourable and aesthetic shaping of the cap (8).

23 Claims, 7 Drawing Sheets

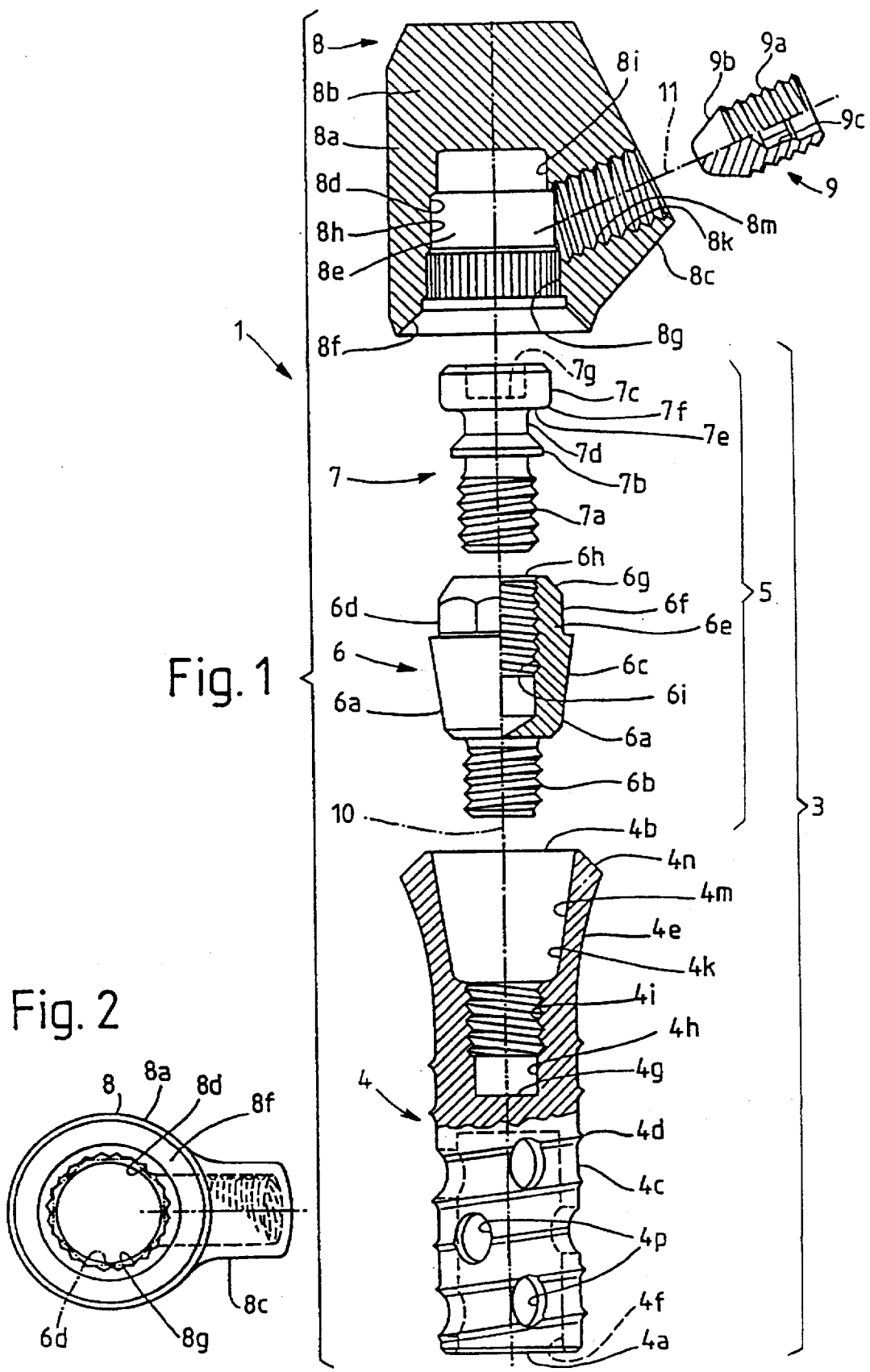

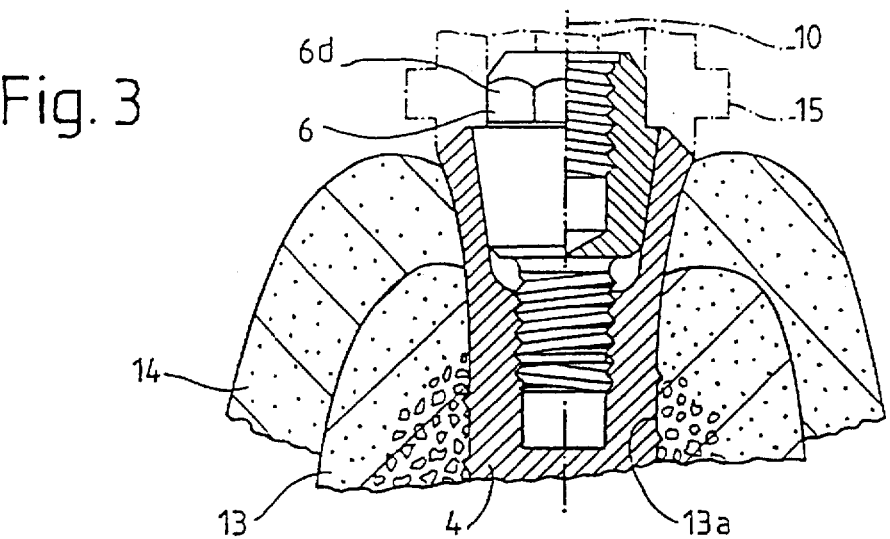
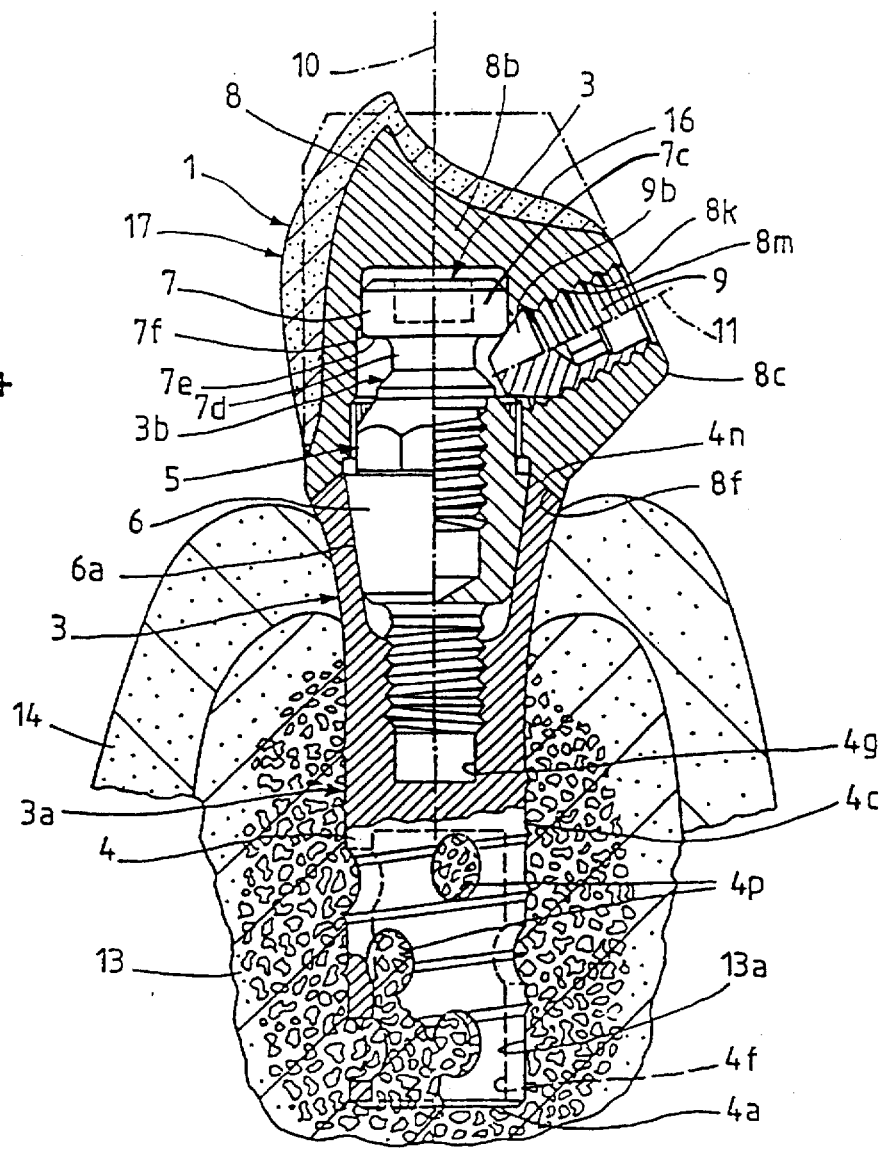

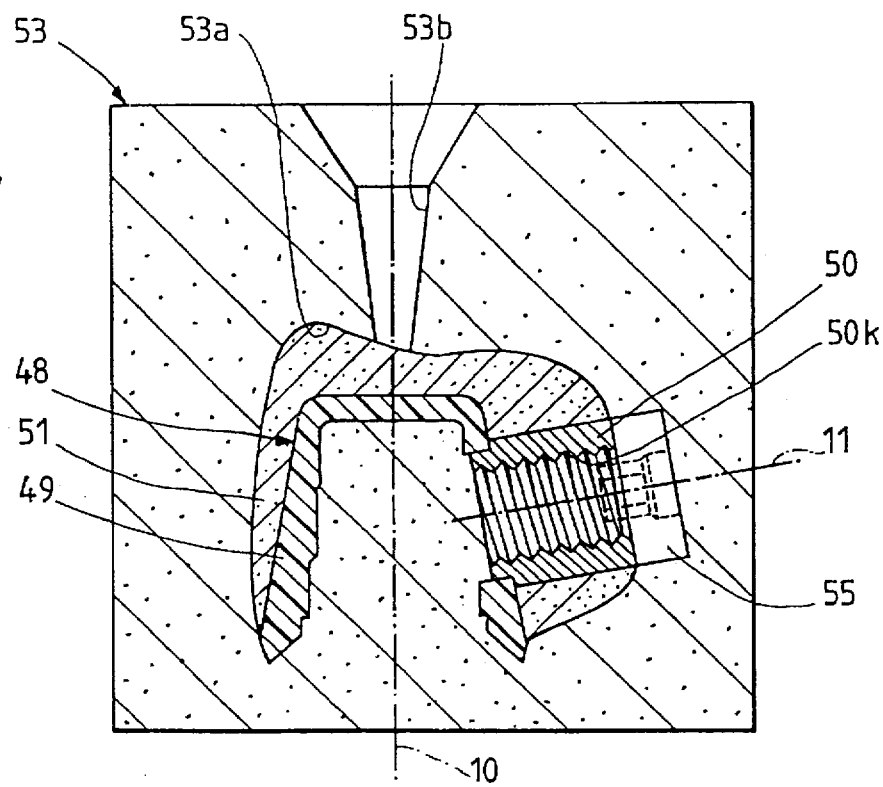
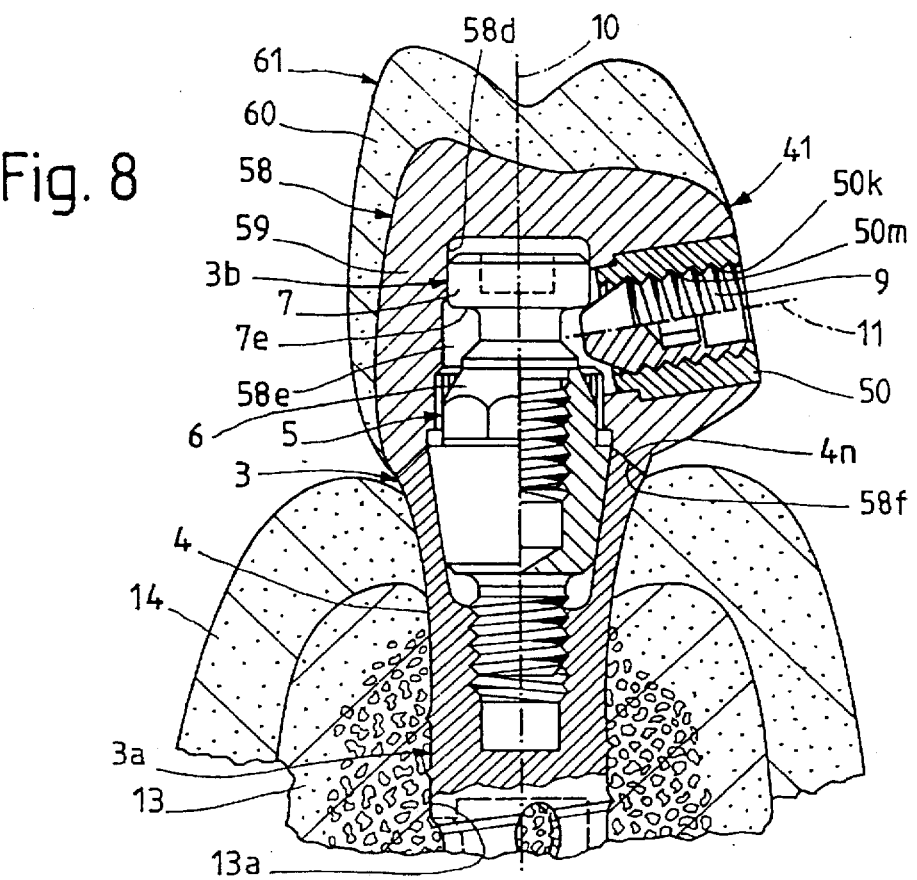

5,667,384

DEVICE FOR FORMING A DENTAL PROSTHESIS AND METHOD OF MANUFACTURING SUCH A DEVICE

BACKGROUND OF THE INVENTION

The invention relates to a device for forming a dental prosthesis.

The dental prosthesis can have only one single artificial tooth or only one artificial dental crown or two or more artificial teeth or dental crowns.

Devices for forming a dental prosthesis known under the ITI mark on the market have a support and a cap which can be fastened thereon and serves to form an artificial dental crown. The support has a base or primary part and a secondary part which can be detachably connected thereto. The base has a first end, which sits in a hole of a jawbone during the use of the device, a second end projecting from the jawbone, an axial hole which opens into this end and has a section with an internal thread. The base has a conical annular surface which surrounds the mouth of the hole and which serves as a bearing surface for the cap. The secondary part serves as a holder for holding the cap and has an inner part which is screwed into the hole of the base, an octagonal head situated outside the base, and an axial threaded hole opening into the end face of the head. The cap consists of a gold alloy and has a conical countersurface which rests on the conical bearing surface of the base and a hole which is coaxial with the axis of the support and the countersurface of the cap. The cap is fastened on the secondary part with a screw which penetrates the hole and is screwed into the threaded bore of the secondary part. During use of the device, additional materials are also applied to the originally approximately frustoconical cap so that, together with the materials applied, an artificial dental crown having the desired shape is formed.

In these known devices, the hole of the cap opens in the apical end of the cap facing away from the jawbone. The head of the screw accordingly lies, in an artificial molar, in or below the masticating surface of the crown which is in part formed by the cap. In an artificial incisor or canine, the screw head is situated, for example, below or close next to the cutting part of the dental crown. The hole of the cap and the screw therefore hinder optimum formation of the dental crown. This is the case in particular in incisors. In addition, the screw head is aesthetically disturbing.

The devices known under the mark ITI are used not only for replacing individual teeth but also for fastening and/or forming bridges replacing a number of teeth and in this case have two or more supports, on which a cap is fastened in each case. A connection element forming at least one artificial tooth is arranged between these and connected by cast or soldered connections to the caps which consist of a gold alloy. In order that the caps can be mounted on the octagonal heads of the supports, the axes of the two supports must be reasonably accurately parallel with one another. Accordingly, the holes drilled in the jawbone for receiving the bases must be reasonably accurately parallel with one another so that great accuracy is necessary when drilling these holes.

The aim of the invention is to produce a device having at least one support and at least one cap, which makes it possible to eliminate disadvantages of the known devices, and in particular to avoid the hole of the cap having to be coaxial with the axis of the support and the screw serving for fastening the cap having to have a head lying at the apical end of the cap.

SUMMARY OF THE INVENTION

The aim of the invention is achieved by providing a device for forming a dental prothesis in which the secondary part has a shoulder which faces the end of the support at least when the device has been assembled, the hole of the cap has an internal thread, the screw axis forms an angle with the axis of the device, and the screw has an end section tapering away from its thread and, when the cap is arranged on the secondary part, can be screwed into the internal thread of the cap in such a manner that the end section of the screw engages on the shoulder, and thus generates a force pressing the countersurface of the cap against the bearing surface of the support.

BRIEF DESCRIPTION OF THE DRAWINGS

The subject of the invention is explained below with reference to exemplary embodiments illustrated in the drawing, in which FIG. 1 shows an exploded illustration of parts of a device for fastening and forming a dental prosthesis with a single artificial tooth, FIG. 2 shows a view of the cap of the device visible in FIG. 1 from below, FIG. 3 shows a section through a jawbone and parts of the device visible in FIG. 1, FIG. 4 shows a section through the jawbone and, fastened thereon, the device with a finished, artificial dental crown, FIG. 7 shows a section through a casting mould which surrounds the cap visible in FIG. 6, FIG. 8 shows a section through a jawbone and, fastened thereon, a device with a cast cap.

DETAILED DESCRIPTION OF THE PREFERRED EMBODIMENTS

Figure 5:
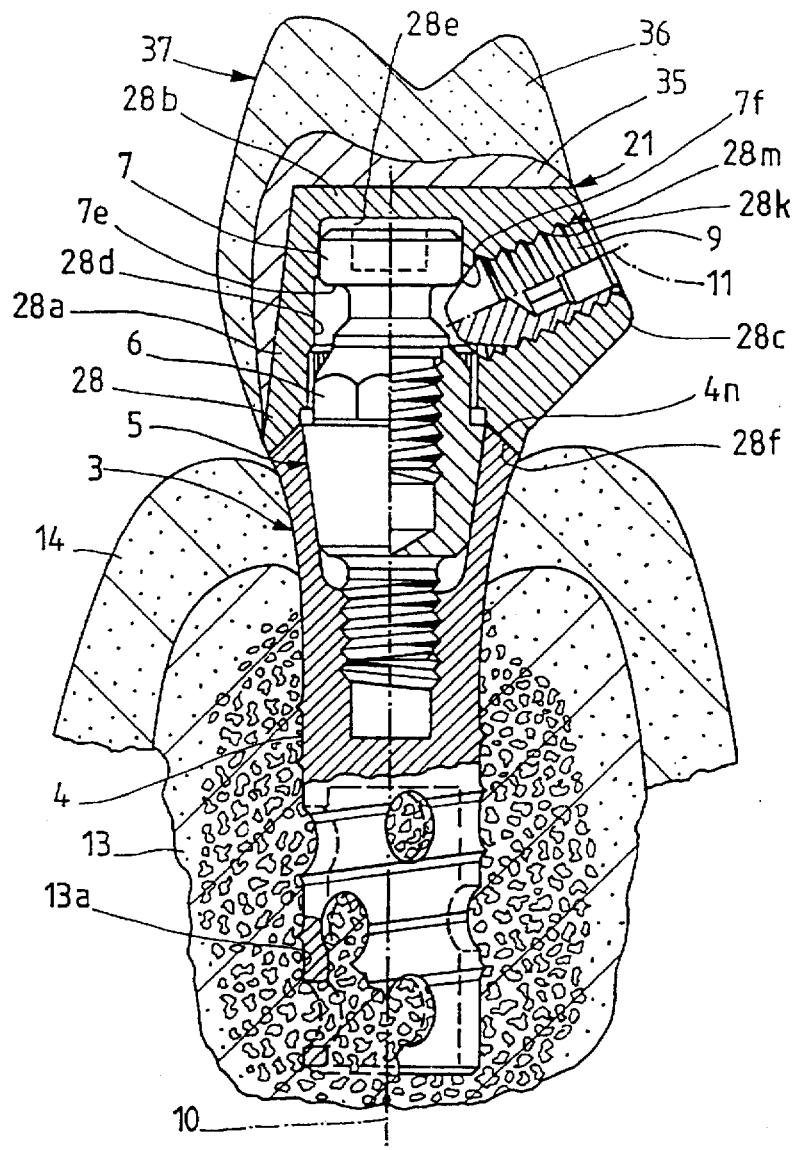
FIG. 5 shows a section through a jawbone and another device fastened thereon.

The device which is shown in FIG. 1 in dismantled state and in FIG. 4 in the assembled end state and is designated as a whole by 1 serves for fastening and forming a dental prosthesis, namely a single artificial tooth. The device 1 has a support 3 with a base 4, frequently also designated as primary part or implant, and a holder 5 which consists of a secondary part 6 and a tertiary part 7. The device 1 also has a cap 8 which, with the aid of a screw 9, can be connected rigidly and detachably to the support 3. The three parts 4, 6, 7 of the support 3 and the cap 8 define in the assembled state a common, first axis 10.

Some parts of the device 1 are also visible in FIGS. 2 and 3. Furthermore, in FIGS. 3 and 4, a jawbone 13—namely a lower jawbone—and the gingiva 14 —i.e. the gum—covering the jawbone of a patient are also drawn. The support 3 has an inner part 3a which in the end state of the device 1 is situated inside the jawbone 13 and an outer part 3b situated outside the jawbone 13.

The elongate, one-piece base 4 has a first end 4a which is situated at the bottom in FIG. 1, and, facing away from this, a second end 4b. The shell surface of the base has a generally cylindrical main section 4c with an external thread 4d and an end section 4e which widens in a trumpet-shaped manner towards the second end 4b. The base has two axial blind holes, namely one hole 4f opening into its first end 4a and one hole 4g opening into its second end 4b. The hole 4g has a cylindrical section 4h with an internal thread 4i and, widening from this towards the second end 4b of the base 4, a section 4k with a cone surface 4m. This forms with the axis 10 an angle amounting to 5° to 15° and for example approximately 8°. The base has at its second end 4b a conical annular surface 4n which surrounds the mouth of the hole 4g and the axis 10 completely and continuously, is rotationally symmetrical in relation to the axis 10, is inclined outwards towards the first end 4a of the base and forms with the axis 10 an angle of approximately or exactly 45°. As will be explained in greater detail, the conical annular surface 4n also serves, in the variant embodiment of the device drawn in FIG. 1, as a bearing surface 4n for the cap 8. Furthermore, the base also has some radial holes 4p which open into the axial hole 4f.

The one-piece secondary part 6 has an inner part 6a which has an external thread 6b and also, widening away from this, a cone surface 6c which forms the same angle with the axis 10 as the cone surface 4m. When, according to FIG. 4, the secondary part 6 is connected to the base 4, the inner part 6a of the secondary part 6 is situated in the hole 4g of the base 4, the external thread 6b being screwed into the internal thread 4i and the cone surfaces 4m and 6c bearing firmly against one another. The secondary part 6 has a head 6d which is situated outside the base 4 when the device 1 has been assembled. This head has a section 6e with a polygonal circumferential surface 6f which is non-rotationally symmetrical in relation to the axis 10 and for example forms in cross-section a regular octagon. This surface accordingly has several, namely eight, plane, circumferential surface sections which are non-rotationally symmetrical in relation to the axis 10 and eight edges parallel to the axis 10. The head 6d also has a conical chamfer 6g which tapers from the circumferential surface 6f towards the end side 6h of the head. The end side 6h of the head 6d forms the outer end of the secondary part, which faces away from the inner part 6a of the secondary part 6. The secondary part 6 is provided with an axial threaded bore 6i which opens into the end face 6h.

The one-piece tertiary part 7 has a bolt-shaped threaded part 7a which is provided with an external thread and is screwed into the threaded bore 6i of the secondary part 6 when the device 1 has been assembled. The tertiary part 7 also has a holding section 7b, which is situated outside the secondary part 6 when the device has been assembled, with a collar which bears with a plane, radial annular surface on a radial, plane annular surface present on the end side 6h of the head 6d. The holding section 7b also has a neck projecting away upwards from the collar and a head 7c. The collar, neck and head 7c together delimit an annular groove 7d surrounding the axis 10. The head 7c has a radial, plane surface adjoining the annular groove 7d and forming the upper flank thereof, a cylindrical circumferential surface and a transition surface which connects the radial, plane surface to the cylindrical circumferential surface and is convexly curved in axial section. The side of the head 7c adjoining the annular groove 7d forms an annular shoulder 7e which runs along the circumference of the support outer part 3b and the outer border 7f of which is formed by the transition surface which is curved in axial section. The shoulder 7e faces the base 4 and its second end 4b when the device 1 has been assembled. The transition surface forming the outer border 7f of the shoulder 7e has in axial section a radius of curvature which amounts to 0.5 mm at most, preferably 0.3 mm at most and for example approximately 0.2 mm. It is to be noted that, instead of the curved transition surface or if appropriate in addition to this, the outer border 7f of the shoulder 7e could have an edge. The head of the tertiary part 7 has a polygonal and/or star-shaped hole 7g opening into its end side.

The one-piece cap 8, which is also shown separately in FIG. 2, has a shell 8a and a compact, apical end section 8b which is hole-free in particular in the region of the axis 10 and faces away from the base 4 when the device 1 has been assembled. The cap 8 is generally rotationally symmetrical in relation to the axis 10 but has a nose 8c which projects to the right in FIGS. 1, 2 and 4. The cap 8 has an inner surface 8d which delimits an inner space 8e which is generally rotationally symmetrical in relation to the axis 10 and open towards the base 4. The section of the inner surface 8d adjoining the mouth of the inner space 8e forms a conical countersurface 8f which is inclined away from the mouth towards the axis 10, surrounds the axis 10 completely and continuously, forms with this the same angle as the annular and/or bearing surface 4n of the base 4 and bears against the conical annular and/or bearing surface 4n when the device has been assembled. The two conical surfaces 4n and 8f have external diameters of the same size so that the outer and/or shell surfaces of the base 4 and of the cap 8 abut at the outer borders of the conical surfaces 4n and 8f when the device 1 has been assembled. The inner surface 8d has, on the side of the countersurface 8f facing away from the mouth of the inner space 8e, a polygonal inner surface region 8g which is non-rotationally symmetrical in relation to the axis 10 and for example 24-cornered in cross-section. This region therefore has several, namely 24, plane, non-rotationally symmetrical surface sections parallel to the axis 10 and 24 corners or edges parallel to the axis 10. In FIG. 2, the outline of the head 6d is also indicated in dot-dash lines. This is designed in such a manner that the corners of its octagonal section 6e engage snugly or with at most small radial play in corners of the 24-cornered inner surface region 8g. The inner surface 8d has, above the 24-cornered inner surface region 8g, a cylindrical inner surface section 8h, which is adjoined by a likewise cylindrical, slightly narrower inner surface section 8i. The diameter of the latter is at most slightly greater than the diameter of the head 7c of the tertiary part 7. When the cap 8 is pushed onto the support 3 parallel to the axis 10 during assembly of the device 1, it is guided axially displaceably and radially at least approximately without play by the heads 6d and 7c of the secondary part 6 and tertiary part 7 respectively. The surface sections and the edges of the circumferential surface 6f which is non-rotationally symmetrical in relation to the axis 10 and of the inner surface region 8g form in addition securing means which secure the cap 8 against rotations with regard to the secondary part 6 of the support 3 when the device has been assembled. When the device 1 has been assembled, according to FIG. 4, an interspace is present between the end surface of the head 7c of the tertiary part 7 and the inner surface section of the cap 8 delimiting the upper end of the inner space 8e. The cap 8 has a hole 8k which extends through the nose 8c into the inner space 8e and the outer mouth of which lies in a surface of the nose 8c which is inclined in relation to the axis 10 and the inner mouth of which lies mainly in the region of the cylindrical inner surface section 8h of the cap. The hole 8k is provided with an internal thread 8m. The hole 8k surrounds and defines a second axis 11. The hole 8k and the section of the axis 11 situated in it are inclined away upwards from the axis 10 and thus away from the base 4. The second axis 11 forms with the first axis 10 an angle which amounts to at least 30°, preferably at least 45°, less than 90°, for example 55° to 85° and namely according to FIGS. 1, 4 approximately 65°. The hole 8k and the screw 9 screwed into it when the device 1 has been assembled are thus to a greater or lesser extent transverse to the axis 10.

The screw 9 has a thread 9a and, tapering away from this, a for example approximately frustoconical end section 9b. The conical surface of the latter forms with the screw axis, which coincides with the axis 11 of the hole 8i when the device 1 has been assembled, an angle which amounts to at most 60°, preferably at most 45° and for example approximately 30°. The screw 9 is designed as a headless screw and thus has no head so that the nominal or external diameter of its thread 9a forms the maximum diameter of the screw 9. This has, at its end facing away from the end section 9b, a hole 9c which has a polygonal, for example hexagonal, section, the surfaces and edges of which form driving means for a screwing-in tool. The nominal or external diameter of the thread 9a amounts preferably to at least 1.5 mm and for example approximately or exactly 2 mm. The overall length of the screw 9 is at most three times and for example approximately twice the size of the nominal or external diameter of the thread 9a.

When the device 1 has been assembled, the screw 9 is according to FIG. 4 screwed into the hole 8k of the cap 8 in such a manner that the conical surface of the end section 9b of the screw 9 engages on the outer border 7f of the shoulder 7e of the tertiary part 7. At its point touching the shoulder 7e, the conical surface of the screw 9 forms with the axis 10 an angle which amounts to preferably at least 30°, preferably at most 60° and for example according to FIG. 4 approximately 35°. When the screw 9 has been screwed in firmly, the shoulder 7e of the tertiary part 7 exerts a force on the screw and via this on the cap 8. This force has a component which is parallel to the axis 10 and which presses the countersurface 8f of the cap 8 against the bearing surface 4n of the base 4 and clamps the cap 8 firmly on the support 3. The screw 9 is situated completely inside the cap 8 when the device 1 has been assembled and finished.

The base 4, secondary part 6, tertiary part 7, the cap 8 and the screw 9 consist of biocompatible metal materials. The base 4, the secondary part 6 and the tertiary part 7 and the cap 8 consist for example of pure titanium. The outer surface of the cylindrical main section 4c of the base 4 can be formed by a porous coating likewise consisting of titanium which is applied by plasma spraying. The screw 9 is formed for example from an alloy consisting mainly of titanium and is harder than the cap 8. When the screw 9 is tightened during assembly of the device 1, the screw 9 can produce an indentation in the outer border 7f of the shoulder 7e. This indentation secures the cap 8 in addition to the polygonal circumferential surface 6f of the secondary part 6, which engages on the polygonal inner surface region 8g, against rotations with regard to the support 3.

The manufacture, use and also the assembly of the device 1 in the fastening and formation of an artificial dental prosthesis are now also to be explained. First, the parts of the device 1 drawn in FIG. 1 are manufactured in a manufacturing factory and supplied, for example in demounted state, to a dentist and/or dental technician.

If the dentist wishes to use the device 1 in the treatment of a patient, the dentist can cut open the gingiva 14 of the patient, drill and/or mill a hole 13a into the jawbone 13, screw the base 4 into this and close the upper axial hole 4g of the latter with a closure screw (not shown) screwed into it. The base 4 can then remain in the jawbone 13 for a taking period until the jawbone has healed. The bone can subsequently fill the lower axial hole 4f and also penetrate the radial holes 4p so that the base is anchored vary stably in the jawbone 13.

After the taking period, the dentist can unscrew the closure screw from the base 4, screw the secondary part 6 into the latter and fasten an impression cap 15, indicated in dot-dash lines in FIG. 3, on the secondary part 6. The dentist can then make an impression with a plastically deformable material which is pressed onto the jaw, onto the impression cap 15 and onto the teeth adjacent to the latter with a so-called tray.

Figure 6:
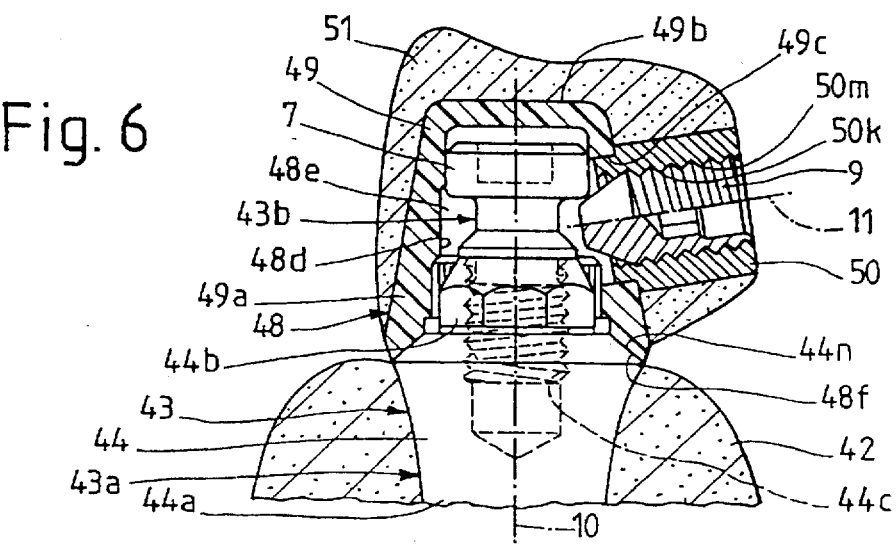
FIG. 6 shows a section through a jaw model of one and parts of another device, the cap of which has a sleeve made of plastic.

A dental technician can then produce a model of a jawbone from plaster or the like and provide it with a handling support which is of the same design as the handling support 43 drawn in FIG. 6 which serves for forming another device and is described in greater detail. The dental technician can fasten the cap 8 on the handling support and bring the cap 8 into a desired shape on the basis of the impression by material-removing finishing—i.e. by milling and/or grinding. The original outline shape and the outline shape of the cap 8 existing after finishing are shown in FIG. 4 with dot-dash and solid lines respectively. It is to be noted that the section of the nose 8c delimiting the outer mouth of the hole 8k is drawn in FIG. 4 with the original shape but if necessary can also be further worked, it being possible to mill off and/or grind off a section of the screw 9 as well. The dental technician can also provide the outer surface of the cap 8 partially with a veneer 16 which can be seen in FIG. 4 and consists for example of ceramic (porcelain) or plastic. The cap 8 then forms together with the veneer 16 a supraconstruction 17, namely an artificial dental crown.

The secondary part 6, which is connected to the jawbone 13 of the patient by the implant 4, can be closed for example with a closure element during the working of the cap 8 to form a supraconstruction 17 or artificial crown. When the crown is finished, the dentist can first screw the tertiary part 7 into the secondary part 6.

The cylindrical main section 4c of the base 4 and the lower end section of the secondary part 6 then form the inner part 3a of the support 3 situated in the jawbone 13. The first end 4a of the base 4 forms in this connection the end of the support 3 situated on the jawbone. Furthermore, the second end 4b of the base 4, the upper section of the secondary part 6 and the tertiary part 7 together form the outer part 3b of the support 3 situated outside the jawbone 13. The end of the support 3 situated outside the jawbone is formed by the head 7c of the tertiary part 7. The secondary and the tertiary part together form the holder 5 of the support 3, which serves for holding the supraconstruction 17 or dental crown.

The dentist can then also mount the supraconstruction 17 or dental crown formed from the finished cap 8 and the veneer 16, together with the screw 9 which has already been screwed a little into the cap 8, on the outer part 3b of the support 3, screw the screw 9 firmly with a screwing-in tool and thus fasten the cap 8 forming the majority of the supraconstruction 17 on the support 3. The dental crown shaped according to FIG. 4 can for example form together with the remaining parts of the device 1 an artificial incisor or canine. The finished end section 8b of the cap 8 facing away from the base 4 and the jawbone 13 and the veneer 16 applied to the end section 8b together form the apical end and the cutting part of the artificial dental crown. The cutting edge of the cutting part is situated on the side of the axis 10 facing away from the nose 8c of the cap 8. Furthermore, the nose 8c, the mouth of the hole 8k lying in this and thus essentially the entire hole 8k and also the screw 9 are situated—in relation to the mouth of the patient—on the rear side of the cap 8 so that the hole 8k and the screw 9 are not visible from the outside of the mouth. As the hole 8k and the greater are to a greater or lesser extent transverse to the axis 10, the shape of the apical end, facing away from the jawbone 13, of the supraconstruction 17 or artificial dental crown can be favourably established and extensively adapted to the shape of a natural tooth.

The octagonal circumferential surface region 6f of the secondary part 6 and the 24-cornered inner surface region 8g of the cap 8 make it possible to mount the latter optionally in 24 different rotary positions on the support 3 and to connect it unrotatably thereto. The relatively great number of selectable rotary positions of the cap 8 makes it possible to insert it into the mouth of the patient in such a manner that the nose 8c and the hole 8k are situated in a position which is expedient for screwing firm the screw 9. As the hole 8k is inclined away from the jawbone in the direction running away from the axis 10, the dentist can screw the screw 9 firm relatively well although the hole 8k is arranged on the rear side of the cap 8.

When the device 1 has been assembled according to FIG. 4 and is fastened in the jawbone 13, the various parts of the support 3, i.e. the base 4, the secondary part 6 and the tertiary part 7 are stably interconnected. The support 3 has great strength. The outer part 3b of the support 3 centres the cap 8 or—more precisely—its inner space 8e in relation to the support 3 and secures the cap 8 against rotations about the axis 10 also. The conical countersurface 8f of the cap bearing on the conical bearing surface 4n of the base 4 likewise has the effect of centring the cap in relation to the base 4. The cap 8 is connected very stably to the support 3 and can therefore transmit to the support both great forces parallel to the axis 10 and great forces forming an angle with the axis 10. Because the screw 9 has a relatively great diameter, is quite short in comparison with this and engages at a point on the shoulder 7e of the tertiary part 7 situated close to the hole 8k of the cap 8 holding the screw 9, the risk of the screw 9 breaking is also very low.

As a result of the conical surfaces 4n and 8f which bear on one another and the shell surfaces of the base 4 and of the cap 8 which abut without a gap at the outer borders of the conical surfaces, it is additionally practically completely prevented that cultures of microorganisms develop between the base 4 and the cap 8. Furthermore, the very good biocompatibility of titanium is also advantageous.

The device 1 has only relatively few separate parts and can be economically manufactured and also relatively easily inserted into the mouth of a patient and assembled. Furthermore, a dental technician can, from the cap 8 consisting of titanium which can be seen in FIG. 1 and is supplied from the manufacturing factory, manufacture an artificial dental crown adapted to the individual requirements of a patient with relatively low labour and material expenditure.

In FIG. 5, a jawbone and a gingiva can be seen, which are again designated with 13 and 14 respectively. Furthermore, in FIG. 5, an assembled device 21 can be seen, which is fastened on the jawbone 13, situated in its end state and forms a dental prosthesis serving as an artificial molar. The device 21 has a support 3 which is of identical design to the support 3 of the device 1. The support 3 has in particular a base 4, fastened in a hole 13a of the jawbone 13, with a conical annular and bearing surface 4n, and a holder 5 with a secondary part 6 and a tertiary part 7. The device 21 also has a cap 28 which has a common first axis 10 together with the support 3 when the device has been assembled. The cap 28 has, like the cap 8, a shell 28a, an end section 28b facing away from the base 4, and a nose 28c projecting away from the shell 28a at a circumferential point thereof. The cap 28 differs from the cap 8, however, in that its shell 28a is generally—i.e. apart from the nose 28c—not cylindrical but conical and tapers away from the base 4. Furthermore, the dimension of the end section 28b of the cap 28 measured parallel to the axis 10 is smaller than in the cap 8. Furthermore, the cap 28 does not consist of titanium but of a non-oxidizing metal material which can be cast on, for example a gold alloy available under the trade name CERAMICOR. The inner surface 28d and the inner space 28e of the cap 28 delimited by this surface are for example of the same design as in the cap 8. The inner surface 28d has in particular at the mouth of the inner space a section which forms a conical countersurface 28f which bears on the conical bearing surface 4n of the base when the device 21 has been assembled. The cap 28 also has a hole 28k which opens into the inner space 28e similarly to the hole 8k, has an internal thread 28m and defines a second axis 11. Screwed into the hole 28k is a screw 9 which is of the same design as in the device 1 and, similarly to this case, engages on the outer border 7f of the shoulder 7e of the tertiary part 7.

The cap 28 is supplied to a dentist and/or dental technician from the manufacturing factory with the shape drawn in FIG. 5. In the use of the device 21, a dental technician can apply a carrier layer 35 to regions of the outer surface of the cap 28. The carrier layer 35, which forms a so-called supporting structure, can for example consist of a gold alloy which is cast onto the cap 28 and oxidizes in the presence of oxygen and onto which a veneer 36 consisting of ceramic or plastic is applied. The cap 28 then forms together with the carrier layer 35 and the veneer 36 a supraconstruction 37, namely an artificial dental crown, the apical end of which, which faces away from the jawbone 13 and base 4, can form for example the masticating surface of a molar.

The device 21 is—provided nothing else has been indicated previously—of similar design to the device 1 and also to a great extent has similar properties to it.

Next, with reference to FIGS. 6, 7 and 8, the manufacture and design of a device 41 forming an artificial single tooth, which can be seen in the finished state in FIG. 8, will be described. In FIG. 6, a jaw model 42 consisting for example of plaster can be seen, the upper part of which for example has approximately the same outline shape as the jawbone, covered by the gingiva, of a patient. Also drawn in FIG. 6 is a handling support 43 with an inner part 43a situated inside the jaw model 42 and an outer part 43b situated outside the jaw model. This has a one-piece handling implant 44 with a base 44a which is fastened in the jaw model 43 and the upper region of which has the same shape as the upper end section of a base 4. The lower region of the base of the handling implant 44, which cannot be seen in FIG. 6, can on the other hand have a different shape from the corresponding section of the base 4, as is indicated in the handling implant 44 drawn in FIG. 11 which serves for forming another device. The handling implant 44 also has a head 44b which is situated outside the jaw model 43 and has the same shape as the head 6d of a secondary part 6. The handling implant 44 is additionally provided with a threaded bore 44c corresponding to the threaded bore 6i of a secondary part 6. The handling implant has a conical annular and/or bearing surface 44n which is of similar design to the annular and/or bearing surface 4n of a base 4. The handling support 43 also has a tertiary part 7 screwed detachably into the threaded bore 44c of the handling implant 44.

In FIG. 8, a jawbone 13 with a hole 13a and the gingiva 14 of a patient can be seen. Furthermore, drawn in FIG. 8 is the support 3 belonging to the device 41, which is of the same design as in the devices 1 and 21. The support 3, which has an inner part 3a and also an outer part 3b, therefore again has a base 4 with a conical annular and/or bearing surface 4n and a holder 5 with a secondary part 6 and a tertiary part 7 which has a shoulder 7e.

The manufacturing factory manufactures, in addition to the parts of the support 3 visible in FIG. 8, the parts visible in FIG. 6 of the handling support 43 already described and a cap 48 visible in FIG. 6. The latter has a sleeve 49 and a bushing 50. The sleeve 49 has a shell 49a and, on the end of this situated at the top in FIG. 6, a plane end section 49b. The shell 49 has for example an outer surface which tapers conically towards the end section 49b. The shell 49a of the sleeve is provided with a hole 49c, in which one end of the bushing 50 is fastened by a press and/or adhesive connection. The inner surface of the sleeve 49 forms the major part of the inner surface 48d of the cap 48. The inner surface 48d and the inner space 48e of the cap 48 have essentially—i.e. apart from the differences caused by the hole 49c and the bushing 50—the same shapes and dimensions as the inner surface 8d and the inner space 8e of the cap 8. The cap 48 also has in particular a conical countersurface 48f which in FIG. 6 bears on the conical annular and/or bearing surface 44n of the handling implant 44. The bushing 50 has a generally cylindrical outer surface, the end section of the bushing sitting in the hole 49c of the sleeve 49, however, having a smaller external diameter than the rest of the bushing. The bushing 50 has a continuous hole 50k with an internal thread 50m. The hole 50k defines the axis 11.

The sleeve 49 consists of a material which can be burned without solid residues, namely a plastic, for example of a polyoxymethylene copolymer. The bushing 50 consists of an unburnable metal material, for example of a non-oxidizing gold alloy, onto which another gold alloy can be cast.

When a dentist wishes, using a cap 48, to fasten and form an artificial dental prosthesis, he first inserts a base 4 into the jawbone 13. After the base 4 has taken, the dentist can screw a secondary part 6 into the base 4, fasten an impression cap corresponding to the impression cap 15 drawn in FIG. 3 on the secondary part 6 and make an impression. A dental technician can then form the jaw model 42 drawn in FIG. 6 and provide it with the handling support 43 supplied from the manufacturing factory. The dental technician can then fasten the cap 48 supplied from the manufacturing factory detachably on the handling support 43 by means of a screw 9. The dental technician can also apply an at least temporarily plastically deformable modelling material 51 which for example can be melted and/or burned without solid residues—for example wax or plastic—to the cap 48 and, using the impression produced in the mouth of the patient by the dentist, shape the modelling material 51 into a superstructure body, for example plastically deform it in a halfsolid state and/or grind it after solidification. Then the dental technician undoes the screw 9, takes the cap 48 provided with modelling material 51 from the handling support 43 and screws the closure screw 55 visible in FIG. 7 into the bushing 50. The closure screw 55 has a threaded part which fills the hole 50k of the bushing 50 and a head situated outside the bushing 50. The dental technician then forms, from a pasty embedding compound which consists of powder and water and sets after a given period of time, a casting mould 53 which can be seen in FIG. 7 and surrounds the cap 48 provided with the modelling material 51 and also fills the inner space of the sleeve 49. The casting mould 53 then delimits an inner space 53a filled by the cap 48 and the modelling material 51 and is also provided with a hole 53b which opens into this space from outside. After the embedding compound has set, the casting mould 53 is heated so that the sleeve 49 consisting of plastic burns and the modelling material 51 melts and also flows out of the casting mould through the hole 53b and/or likewise burns. The inner space 53a of the casting mould 53 then contains only the bushing 50 which is closed with the closure screw 55 and anchored in the casting mould. Then a liquid or at least free-flowing casting material, which can be cast onto the bushing 50 and for example consists of a gold alloy, is introduced through the hole 53b into the inner space 53a of the casting mould 53. The casting material then fills the inner space 53a of the casting mould 53, is cast onto the bushing 50 and solidifies. In this connection, the cap 58 visible in FIG. 8 is produced, which consists of the cast body 59 formed from the solidified casting material and the bushing 50 connected firmly thereto. The casting mould 53 can then be destroyed, i.e. divided into pieces, and the cap 58 can be separated from the casting mould 53. The cap 58 then has an inner surface 58d and an inner space 58e delimited by this. The inner surface 58d and the inner space 58e then have at least approximately the same shapes and dimensions as the inner surfaces 8d, 48d and the inner spaces 8e, 48e respectively. The cap 58 also has in particular a conical countersurface 58f.

The cap 58 can if necessary, after the casting of the cast body 59, also be ground. Furthermore, a veneer 60 consisting of ceramic or plastic can be applied to the outer surface of the cap 58 so that the cap 58 and the veneer 60 together form a supraconstruction 61, namely an artificial dental crown. This is for example designed to replace a molar and provided with a masticating surface but could also serve to replace an incisor or canine. The dentist can mount the cap 58 on the support 3 anchored in the jawbone 13 and fasten it on the support 3 with a screw 9 which engages on the shoulder 7e of the tertiary part 7 of the support 3. The cap 58 then bears with its conical countersurface 58f on the bearing surface 4n of the base 4.

The common axis 11 of the bushing 50 and screw 9 can, with the axis 10 of the handling support 43 and also the cap 48 or of the support 3 and also the cap 58, form an angle which is somewhat greater than the angle formed by the axes 10 and 11 in the devices 1 and 21 and for example amounts to approximately 80°. The conical surface of the screw 9, at its point touching the shoulder 7e of the handling support 43 or of the support 3 fastened in the jawbone 13, forms with the axis 10 an angle which amounts to at least 45° and for example approximately 55°.

Figure 9:
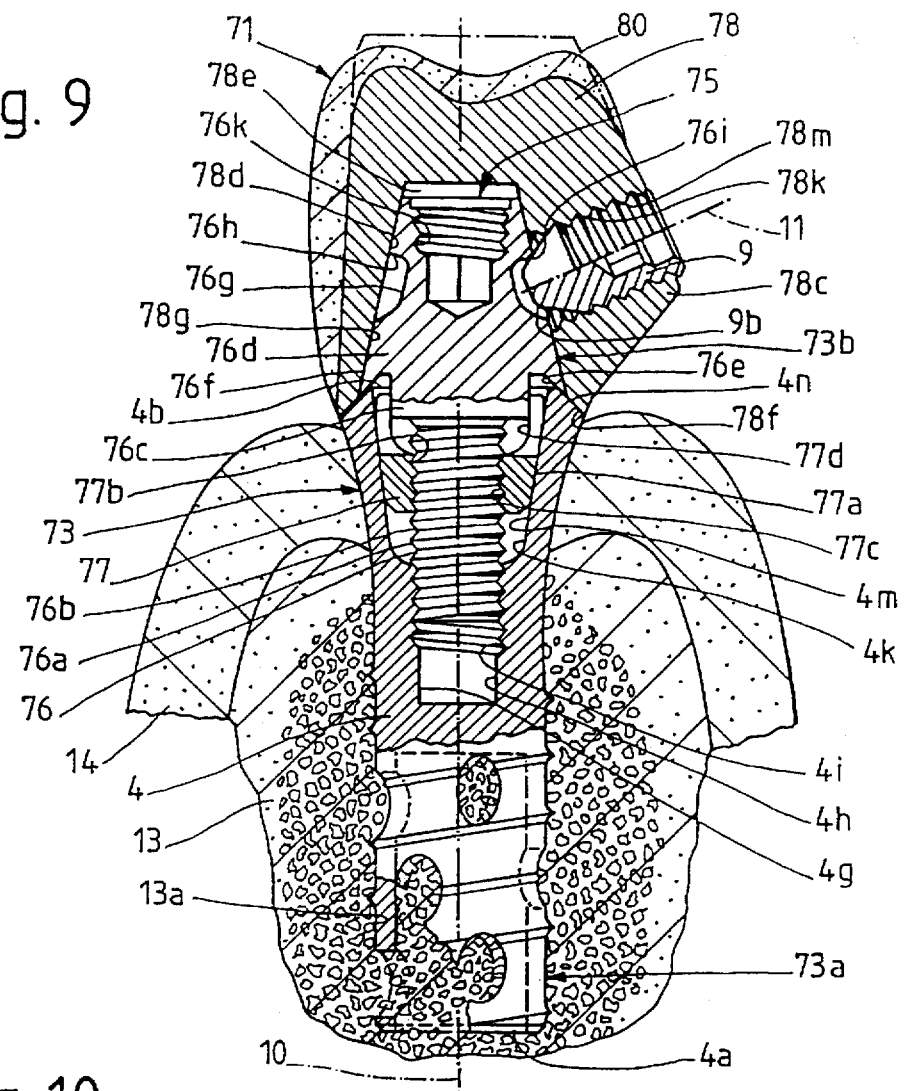
FIG. 9 shows a section transversely through a jawbone and through the axis of a support of, fastened thereon, a device with a bridge.
Figure 10:
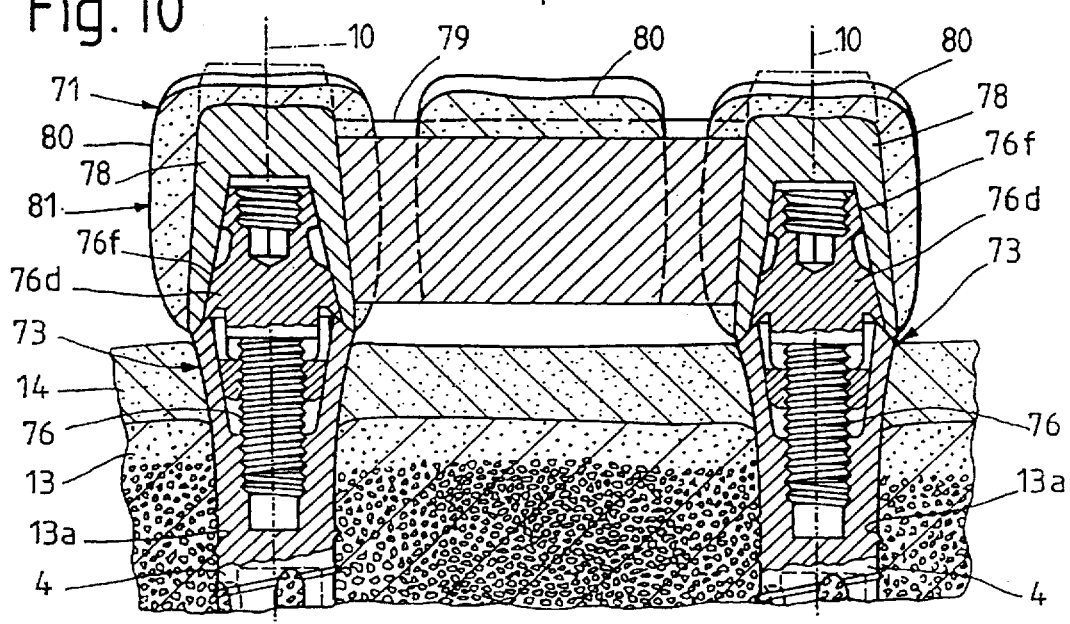
FIG. 10 shows a longitudinal section through a piece of the jawbone visible in FIG. 9 and through the bridge fastened thereon.

The jawbone 13 drawn in FIGS. 9 and 10 is provided with two holes 13a located at a distance from one another along the jawbone 13 and covered by the gingiva 14. The device 71 visible in FIGS. 9 and 10 serves for fastening and forming an artificial dental prosthesis which forms several, namely at least three, artificial teeth. The device 71 has two supports 73 each with an axis 10. Each support has an inner part 73a arranged in the jawbone 13 and an outer part 73b situated outside the jawbone. Each support has a base 4 which is anchored in one of the holes 13a and which is essentially of the same design as in the previously described devices 1, 21 and 41. The base 4 has in particular a first end 4a located in the jawbone 13, a second end 4b situated outside the jawbone, and an axial hole 4g with a cylindrical section 4h having an internal thread 4i, and an extension 4k having a cone surface 4m. Furthermore, the base 4 again has a conical annular and/or bearing surface 4n.

Each support 73 has a holder 75 which has two separate parts, namely a one-piece secondary part 76 and a one-piece sleeve 77. The secondary part 76 has an inner part 76a which is situated in the hole 4g of the base 4 when the device 71 has been assembled. The inner part 76a consists mainly of a bolt-shaped threaded part with an external thread 76b. The inner part 76a has above the threaded part a cylindrical thickening 76c. The secondary part 76 moreover has a head 76d situated outside the base 4 when the device 71 has been assembled. This head forms, at its end adjoining the inner part 76a, a shoulder, the outer region of which is formed is a conical annular surface 76e. This is inclined away from the axis 10 towards the second end 4B of the base 4, forms with the axis 10 an angle of the same size as the conical annular and/or bearing surface 4n of the base 4 and bears on the annular and/or bearing surface 4n when the device 71 has been assembled. The external diameter of the annular surface 76e is, however, smaller than the external diameter of the annular and/or bearing surface 4n so that the annular surface 76e covers only an inner region of the surface 4n. The head 76d has a conical outer surface 76f which tapers away from the inner part 76a and forms, with the axis 10 which it surrounds, a smaller angle than the annular surface 76e and also the annular and/or bearing surface 4n. The head 76d also has an annular groove 76g which surrounds the axis 10 and divides the conical outer surface 76f. The flank of the annular groove 76g further removed from the inner part 76a forms a shoulder 76h. The outer border 76i of the shoulder 76h can, like the outer border 7f of the shoulder 7e, be formed by a transition surface which is curved convexly in axial section and has a small radius of curvature or by an edge. The secondary part 76 also has an axial hole 76k, namely a blind hole opening into the end side of the head 76d facing away from the inner part 76a with a polygonal or star-shaped section, and a section having an internal thread.

The sleeve 77 of the holder 75 has an outer surface which consists mainly of a cone surface 77a. The cone surface 77a forms with the axis 10 the same angle as the cone surface 4m of the base 4. The outer surface of the sleeve 77 can if appropriate also have at its upper end a section which is cylindrical at least before the assembly of the device. The sleeve 77 has an axial, continuous hole 77b, the lower section of which is provided with an internal thread 77c. The hole 77b has above the internal thread 77c a widening 77d, in the region of which the shell of the sleeve 77 is divided into a few, for example four, segments by axial slots extending as far as the upper end of the sleeve.

When the device 71 has been assembled, the sleeve 77 is situated in the widening 4k of the hole 4g of the base 4 and bears with its cone surface 77a against the cone surface 4m of the base 4. The inner part 76a of the secondary part 76 penetrates the hole 77b of the sleeve. The external thread 76b of the secondary part 76 is screwed together with the internal thread 77c of the sleeve 77 and screwed through the hole 77b of the sleeve 77 into the internal thread 4i of the base 4 also. Furthermore, the thickening 76c of the secondary part 76 projects into the widening 77d of the hole 77b of the sleeve 77 and spreads the segments thereof apart. The outer surfaces of the segments of the sleeve 77, which originally for example form sections of a cylinder surface, are then at least in part pressed against the cone surface 4m of the base 4. The secondary part 76 is therefore also supported and held via the sleeve 77 against the cone surface 4m of the hole 4g of the base 4.

The device 71 has for each support 73 a cap 78 assigned thereto. This cap consists of a metal material, namely titanium. The cap 78 has a shell and an end section facing away from the base, is to a great extent rotationally symmetrical in relation to the axis 10 of the assigned support 73, but has a nose 78c corresponding to the nose 8c of the cap 8. The cap 78 has an inner surface 78d which is essentially rotationally symmetrical in relation to the axis 10 and delimits an inner space 78e. The mouth section of this is delimited by a conical countersurface 78f which is coaxial with the axis 10 and which bears on the conical annular and/or bearing surface 4n of the base 4 outside the conical annular surface 76e of the secondary part 76 when the device 71 has been assembled. The cap 78 also has a conical inner surface 78g which forms with the axis 10 the same angle as the conical outer surface 76f. The inner surface 78g surrounds the outer surface 76f with very small radial play so that the head 76d of the secondary part 76 centres and also supports the cap 78, but the cap 78 bears with its conical countersurface 78f firmly and without a gap on the bearing surface 4n of the base 4 in spite of any manufacturing inaccuracies.

The cap 78 has a hole 78k with an internal thread 78m, which penetrates the nose 78c and opens into the inner space 78e. A screw 9 is screwed into the hole 78k. The axis 11 of the hole 78k and of the screw 9 again forms an angle with the axis 10. The conical surface of the tapering end section 9b of the screw 9 engages on the outer border 76i of the shoulder 76h of the secondary part 76 when the device 71 has been assembled, so that the cap 78 is pressed against the base 4 and connected firmly to the support 73.

The device 71 has an element 79 which can be seen in FIG. 10, which forms a connecting element rigidly interconnecting the two caps 78 and consists of a metal material which can be welded together with the caps 78, namely titanium. The element 79 consists at least originally of a piece of a profiled bar with a for example approximately heart-shaped profile. The element 79 has end surfaces which fit snugly against the caps 78 and is at its ends rigidly connected to the two caps by laser-welded connections.

The caps 78 are manufactured at the manufacturing factory with the outline shapes which are drawn in part by dot-dash lines and supplied in separated state to a dentist and/or dental technician. Furthermore, the manufacturing factory can also supply to the dentist a profiled bar piece serving for forming at least one element 79. The dental technician working together with the dentist can then manufacture an element 79 from the profiled bar piece and connect it by laser welding to the two caps 78. The dental technician can additionally shape the caps supplied from the manufacturing factory by material-removing working into the caps 78 drawn with solid lines in FIGS. 9, 10. The dental technician can likewise subject the element 79 to material-removing working so that it takes on a shape which is suitable for forming at least one artificial tooth. The dental technician then also covers the caps 78 and the element 79 in places with a veneer 80 consisting of ceramic or plastic. The two caps 78, the element 79 and the veneer 80 then form together a supraconstruction 81, namely a bridge.

The conical outer surfaces 76f of the heads 76d of the secondary parts 76 make it possible, in interaction with the conical inner surfaces 78g of the caps 78, to mount the supraconstruction 81 or bridge on the two supports 73 even when the axes 10 of the supports 73 and the caps 78 assigned to these are not exactly parallel to one another. Otherwise, the device 71 having a bridge has to a great extent similar characteristics as the device 1 having only a single dental crown.

Figure 11:
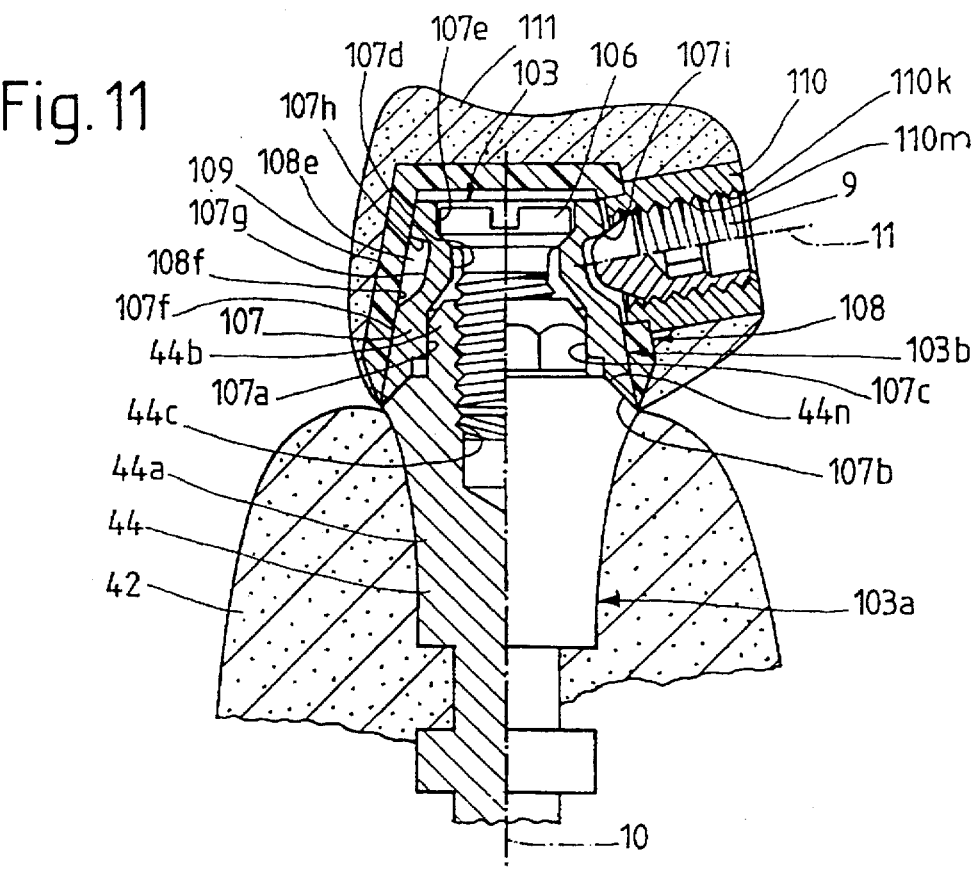
FIG. 11 shows a section through a jaw model of one and through parts of another device which is fastened thereon and serves for forming a bridge.
Figure 12:
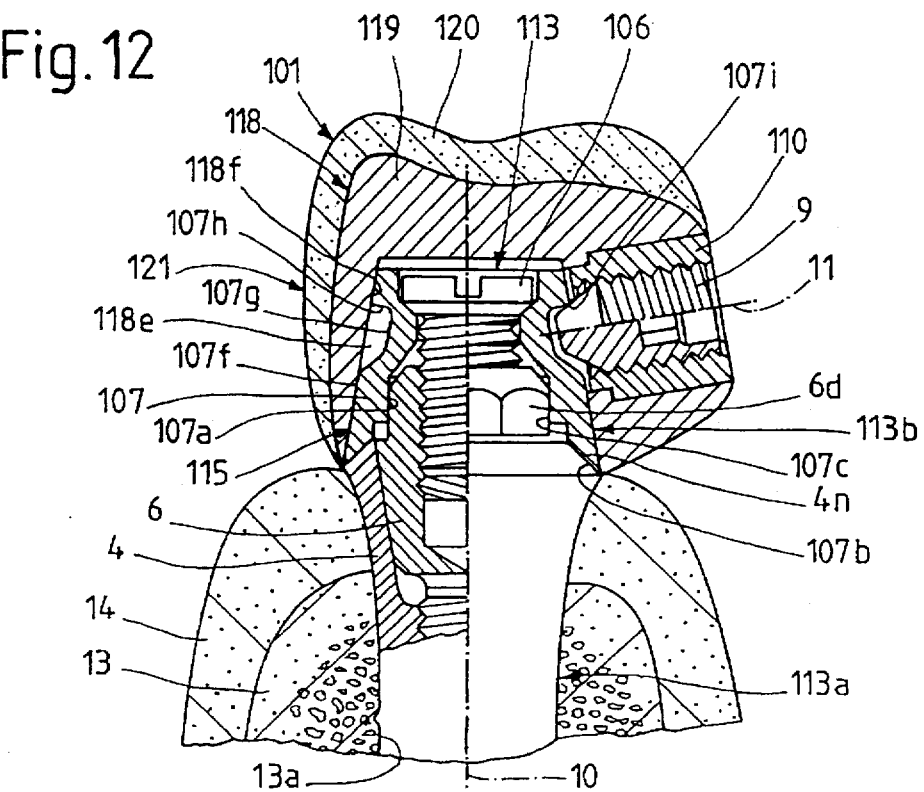
FIG. 12 shows a section through a device manufactured with the aid of the parts illustrated in FIG. 11.

With reference to FIGS. 11 and 12, the manufacture and design of the device 101 visible in the finished state in FIG. 12 will now be described, which like the device 71 serves for forming a dental prosthesis with a number of artificial teeth.

In FIG. 12, in addition to the device 101, a jawbone 13 of a patient and the gingiva 14 covering the jawbone 13 are drawn. For forming and fastening an artificial dental prosthesis, a dentist can provide the jawbone 13 with two holes 13a located at a distance from one another along this jawbone, one of which is visible in FIG. 12. The dentist screws a base 4 into each of these holes 13a, allows this to take, then fastens a secondary part 6 and also an impression cap on each base 4, makes an impression and again removes the impression cap and if appropriate the secondary parts also.

A dental technician then makes, on the basis of the impression, the jaw model which is visible in FIG. 11 and designated by 42 like in FIG. 6 and provides this with two handling supports 103 which are assembled from parts supplied from the manufacturing factory. Each handling support 103 has an inner part 103a arranged in the jaw model 42 and an outer part 103b situated outside the jaw model. Each handling support 103 has a one-piece handling implant 44 which is of the same design as the handling implant drawn in FIG. 6 and accordingly has a base 44a located in the jaw model 42, a head 44b situated outside the jaw model 42, a threaded bore 44c and a conical annular surface 44.

Each handling support 103 defines an axis 10 and has a screw 106 with a threaded part and a head. The handling support also has a sleeve-shaped tertiary part 107 which is fastened detachably on the handling implant 4 with the screw 106 and is coaxial with the axis 10. This part has a continuous, axial hole 107a which, at the mouth situated at the bottom in FIG. 11, is delimited by a conical annular surface 107b which, when the handling support 103 has been assembled, is inclined downwards away from the axis 10, forms with the axis 10 the same angle as the annular surface 44n, has the same external diameter as the annular surface 44n and bears on this. The hole 107a has an inner surface 107c which surrounds the head 44b of the handling implant 44 and which in cross-section is for example octagonal exactly like a section of the head and has eight plane surfaces and edges securing the tertiary part against rotations in relation to the head 44b. The hole 107a has above its octagonal section a narrowing 107d and above this a widening 107e again, which contains the head of the screw 106. The tertiary part 107 has an upwardly tapering conical outer and bearing surface 107f which is divided by an annular groove 107g surrounding the axis 10. The flank of the annular groove 107g further removed from the base 44a forms a shoulder 107h which surrounds the axis 10 and the outer border 107i of which is again formed by a transition surface which is curved convexly in axial section and has a small radius of curvature or by an edge.

The manufacturing factory manufactures and supplies, in addition to the parts of the supports 103, 113, caps 108 which can be fastened on the handling supports 103 and one of which is visible in FIG. 11. Each cap 108 has a sleeve 109 made of a plastic which can be burned without solid residues and a metal bushing 110 consisting of a gold alloy. This bushing is fastened on the sleeve 109 in a similar manner to the bushing 50 on the sleeve 49. The cap 108 has an inner space 108e and a conical countersurface 108f formed by the inner surface of the sleeve 109. This countersurface tapers away from the base 44a, is coaxial with the axis 10 and forms with this the same angle as the outer and bearing surface 107f of the tertiary part 107. The bushing 110 has an axial, continuous hole 110k with an internal thread 110m. The screw 9 screwed into the bushing 110 has together with this a common axis 11, engages with its tapering end section on the outer border 107i of the shoulder 107h and presses the conical countersurface 108f against the conical outer and bearing surface 107f of the tertiary part 107. The border of the cap 108 delimiting the mouth of the inner space 108e extends as far as the outer borders of the conical annular surfaces 44n and 107b.

The dental technician can apply a modelling material 111 to the caps 108 fastened on the handling supports 103. Then, for each cap, a casting mould surrounding this and corresponding to the casting mould 53 visible in FIG. 7 can be manufactured. Furthermore, the sleeves 109 can be burned and the modelling material 111 melted and/or burned. Then a free-flowing casting material, namely a molten gold alloy, can be poured into the inner spaces of the casting moulds and two caps 118 can be manufactured, one of which is visible in FIG. 12 and each of which has a bushing 110 and, cast onto this, a cast body 119 formed from the casting material. Each cap 118 delimits an inner space 118e and has a conical countersurface 118f which surrounds and is coaxial with the axis 10.

The dental technician connects the two caps 118 by means of a connecting element which is not visible in FIG. 12 and which is connected rigidly to the caps for example by means of a casting connection. The caps 118 can be provided with a veneer 120 made of ceramic or plastic and then each form an artificial dental crown. The connecting element consisting for example of a gold alloy can likewise be provided with a veneer and then format least one artificial tooth. The two caps 118 form together with the connecting element a supraconstruction 121, i.e. a bridge.

After finishing the supraconstruction, the dentist can screw the secondary parts 6, which if necessary have previously been unscrewed from the bases 4, into the bases 4 again and fasten a tertiary part 107 on each secondary part 6 with a screw 106. The screw 106 penetrating a tertiary part 107 then presses the conical annular surface 107B of the tertiary part 107 against the conical annular surface 4n of the assigned base 4. Furthermore, the tertiary part 107 is secured by its octagonal inner surface 107c against rotations in relation to the secondary part 6. Each base 4 then forms together with a secondary part 6, a screw 106 and a tertiary part 107 a support 113 with an inner part 113a arranged in the jawbone 13 and an outer part 113b situated outside the jawbone. The secondary part 6, the screw 106 and the tertiary part 107 at the same time together form a holder 115 for holding a cap 118.

The dentist can mount the two caps 118 interconnected by the connecting element on the supports 113 and fasten them on these with screws 9. The screws 9 engaging on the outer borders 107i of the shoulders 107h then generate forces which press the conical countersurfaces 118f of the caps 118 against the conical bearing surface 107f of the tertiary part 107.

The caps 108 and 118 respectively illustrated in FIGS. 11 and 12 do not therefore bear with their conical countersurfaces 108f and 118f respectively on the conical annular surfaces 44n and 4n respectively of the bases 44a and 4 respectively but on the conical bearing surfaces 107f formed by tertiary parts 107.

It would, however, be possible to modify the tertiary parts 107 in such a manner that they bear only on the inner regions of the conical annular surfaces 4n and 44n. Furthermore, the caps 108, 118 could be modified in such a manner that they, similarly to the caps 78 illustrated in FIGS. 9 and 10, bear on the outer regions of the conical annular surfaces 44n and 4n respectively of the bases 44a and 4 respectively with a conical countersurface present at their lower border outside the conical annular surface 107b of the tertiary parts 107. The annular surfaces 44n and 4n of the bases 44A and 4 respectively would therefore then serve both as bearing surfaces for the tertiary parts 107 and as bearing surfaces for the caps 108 and 118 respectively.

On the other hand, the head 76d of the secondary parts 76 visible in FIGS. 9 and 10 could be modified in such a manner that the conical annular surfaces 76e of these secondary parts cover the entire annular surfaces 4n of the bases 4. The conical outer surface 76f of the secondary part heads 76d could then serve as bearing surfaces, on which the caps 78 bear with their inner surfaces 78g which then serve as conical countersurfaces.

Figure 13:
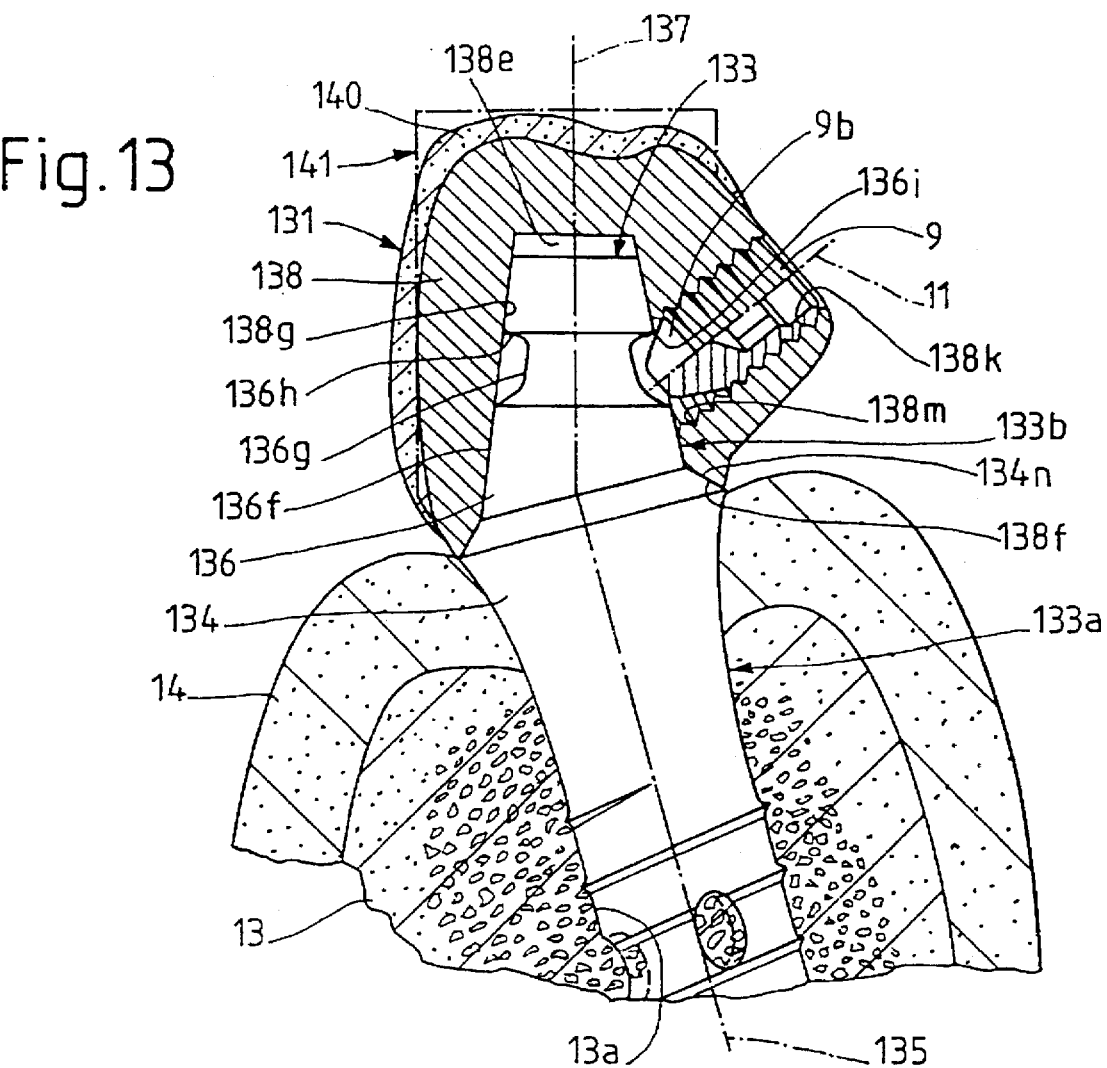
FIG. 13 shows a section through a jawbone and yet another device fastened thereon.

In FIG. 13, a jawbone 13 with a hole 13a can be seen, which is inclined in relation to a vertical because of an anomalous formation of the jawbone or for other reasons. Also visible in FIG. 13 are the gingiva 14 covering the jawbone 13 and a device 131 which for example forms a dental prosthesis having a number of artificial teeth. The device 131 has a support 133 with an inner part 133a and an outer part 133b, said two parts 133a, 133b again being situated inside and outside the jawbone respectively. The base 134 belonging to the support 133 defines an axis 135 coinciding with the axis of the hole 13a, has the same outline shape as the bases 4 and has a first end which is not visible located in the jawbone 13, a second end arranged outside the jawbone 13, and also, situated on this, a conical annular and/or bearing surface 134n which is coaxial with the axis 135 and of similar design to the conical annular and/or bearing surface 4n of the bases 4. The base 134 also has a hole which opens into its second end and which can be designed exactly like the hole 4g of the base 4 or otherwise. The support 133 also has an outer and/or secondary part 136 which is situated outside the jawbone 13 and is fastened rigidly on the base 134 with for example fastening means having a screw which is not visible. The outer and/or secondary part 136 defines an approximately vertical axis 137 which forms an angle with the axis 135. The outer and/or secondary part 136 has a conical outer surface 136f which is coaxial with the axis 137 and tapers conically away from the base 134 and an annular groove 136g surrounding the axis 137. The flank of the groove further removed from the base 134 forms a shoulder 136h, which is coaxial with the axis 137, with an outer border 136i.

The device 131 has a cap 138 with an inner space 138e. The mouth of this facing the base 134 is delimited by a conical countersurface 138f. This is coaxial with the axis 135 and bears on the conical annular and/or bearing surface 134n of the base 134 when the device 131 has been assembled. The majority of the inner space 138e of the cap 138 is surrounded by a conical inner surface 138g which is coaxial with the axis 137. This surface forms with the axis 137 the same angle as the conical outer surface 136f and surrounds the latter with very small radial play when the device 131 has been assembled. The cap 138 also has a hole 138k with an internal thread 138m which opens into the inner space 138e. The hole 138k defines an axis 11 which forms an angle both with the axis 135 and with the axis 137. A screw 9 screwed into the hole 138k engages with the conical surface of its end section 9b on the outer border 136i of the shoulder 136h and thus generates a force which presses the conical countersurface 138f of the cap 138 against the conical annular and/or bearing surface 134n of the base 134.

The cap 138 can consist for example of titanium and be supplied from the manufacturing factory with the outline shape drawn in part by dot-dash lines, be connected for its use by a connecting element to another cap, be milled and/or ground into the shape drawn with solid lines, and be provided with a veneer 140. The cap 138 can then, together with the other cap which is not visible, the connecting element and the veneer 140, form a supraconstruction 141, i.e. a bridge.

The devices can also be modified in other ways. In particular, features of different described devices can also be combined with one another. A supraconstruction serving as a bridge can also for example be provided with caps which are of similar design to the cap 28 and consist of a gold alloy and onto which another gold alloy can then during use be cast by a dental technician, which forms a carrier layer corresponding to the carrier layer 35.

Furthermore, a device can be manufactured, which has more than two, for example three or four supports. The supraconstruction can then have a number of caps corresponding to the number of supports, which caps are rigidly interconnected by connecting elements, mounted on the supports and fastened on these with screws 9.

Furthermore, instead of the support 3, a support with a one-piece body can probably be provided, which has the same outer shape as a base 4 and a secondary part 6 connected thereto or which even forms the holding section 7b of the tertiary part also. The same applies for the supports 73 and 113 and also for the handling supports.

Otherwise, described supports can be fastened on an upper jawbone instead of a lower jawbone so that the lower and upper ends of the supports and of the caps fastened thereon are interchanged in relation to the positions drawn.

We claim:

1. A device for forming a dental prothesis comprising:
   a cap defining an inner space;
   a support for supporting the cap, the cap and the support having a common, first axis; and
   a screw for fastening the cap on the support,
   wherein the support has an inner end for being inserted in a jawbone of a dental prothesis user, and an outer part to be located outside of the jawbone for supporting the cap, the outer part having a bearing surface cooperating with a counter bearing surface of the cap in an assembled condition of the device,
   wherein the cap has a threaded hole for receiving the fastening screw and opening into the inner space, the hole having a second axis extending at an angle to the first axis, and
   wherein the screw has a tapering end section extending, at least partially, into the inner space and engaging a shoulder, which is provided on the outer part and faces the inner part, for generating a pressure force for pressing the counter bearing surface of the cap against the bearing surface of the outer part.

2. A device according to claim 1, wherein the shoulder is annular and extends along a circumference of the outer part.

3. A device according to claim 1, wherein the shoulder has an outer border engageable by the screw end section.

4. A device according to claim 1, wherein the screw is formed of a material which is harder than a material forming the shoulder.

5. A device according to claim 1, wherein the cap has a solid end section remote from the support.

6. A device according to claim 1, wherein the second axis extends outwardly of the support and forms with the first axis an angle between 30° and 90°.

7. A device according to claim 1, wherein the bearing surface of the support and the counter bearing surface of the cap are conical and are inclined outwardly toward the inner end of the support.

8. A device according to claim 1 wherein the support includes:
- an elongate one-piece base having a first end defining the inner end of the support, an outer end opposite the inner end, and a hole formed in the outer end and having a section with an inner thread; and
- a holder having a inner portion receivable in the base hole and provided with an outer thread cooperating with the inner thread of the base hole, and an outer portion for projecting from the base hole.

9. A device according to claim 8, wherein the base hole has a conical section with an outwardly inclined conical surface extending between the section with an inner thread and a mouth of the hole, and the holder has a conical surface bearing against the conical surface of the base hole.

10. A device according to claim 9, wherein the holder comprises a first one-piece part having a head defining the outer portion of the holder and having circumferential surface sections which are non-rotationally symmetrical relatively to the first axis.

11. A device according to claim 10, wherein the first part has an axial threaded bore extending up to an end surface of the head, and wherein the holder further comprises a second one-piece part having a threaded portion, receivable in the axial threaded bore of the first part, and a holding portion projecting out of the head of the first part and having an annular groove defining the outer part shoulder.

12. A device according to claim 10, wherein the cap has inner surface sections, which are non-rotationally symmetrical relative to the first axis, for engaging the circumferential surface sections of the head.

13. A device according to claim 10, wherein the base has conical annular surface surrounding a mouth of the base hole and inclined outwardly relative to the first end;
wherein the holder comprises a second part having a conical annular surface for bearing against the conical annular surface of the base, an annular groove defining the outer part shoulder, and an axial hole; and wherein the device further comprises a screw extendable through the axial bore of the second part and receivable in the axial threaded bore of the first part for connecting the second part with the first part.

14. A device according to claim 9, wherein the base has a conical annular surface surrounding a mouth of the base hole and inclined outwardly relative to the first end; wherein the holder includes a first, one-piece part defining the inner and outer portions of the holder, the outer portion having an annular groove defining the outer part shoulder, a conical annular surface for bearing against the conical annular surface of the base, and a conical outer surface tapering away from the inner portion and forming a smaller angle with the first axis than the conical annular surface thereof; and wherein the holder further includes a second part formed as a sleeve having a conical surface defining the conical surface of the holder bearing against the conical surface of the base hole, and an axial hole having an internal thread, the outer thread of the inner portion cooperating with the internal thread of the sleeve axial hole when the inner portion is received in the base hole.

15. A device according to claim 14, wherein the second part has a conical outer surface defining the bearing surface of the outer part.

16. A device according to claim 8, wherein the base has a conical annular surface surrounding a mouth of the base hole, inclined outwardly relative to the first end and defining the bearing surface of the outer part.

17. A device according to claim 1, wherein the cap is formed of titanium.

18. A device according to claim 17, further comprising a titanium member for supporting an artificial tooth and laser-weldable to the cap.

19. A device according to claim 1, comprising a sleeve formed of burnable material and fastened on the cap, and a metal bushing supported in the cap and forming the threaded hole of the cap.

20. A method of manufacturing a device for forming a dental prothesis, comprising the steps of:
providing a cap defining an inner space;
providing a support for supporting the cap; and
providing a screw for fastening the cap on the support,
wherein the support providing step includes providing a support having an inner end for being inserted in a jawbone of a dental prothesis user, and an outer part to be located outside of the jawbone for supporting the cap and having a bearing surface for cooperating with a counter bearing surface of the cap in an assembled condition of the device,
wherein the cap providing step includes providing a cap having a threaded hole for receiving the fastening screw and opening into the inner space and defining a second axis extending at an angle to a first, common axis of the support and the cap; and
wherein the screw providing step includes providing a screw having a tapering end section for extending, at least partially, into the inner space and for engaging a shoulder, which is provided on the outer part and faces the inner part, for generating a pressure force for pressing the counter bearing surface of the cap against the bearing surface of the outer part.

21. A method according to claim 20, wherein the cap providing step include manufacturing the cap from titanium.

22. A method according to claim 21, wherein the cap providing step further includes laser welding of a titanium element for supporting an artificial tooth to the cap.

23. A method according to claim 20, wherein the cap providing step includes the steps of:
forming a sleeve of a burnable material;
providing a metal bushing having an axial threaded bore and fastening the bushing on the sleeve to form a cap, with the threaded bore forming the threaded hole of the cap;
applying a burnable modelling material on the outside of the cap;
forming a casting mold surrounding the cap and filling an inner space of the sleeve;
burning the sleeve and the burnable material applied on the outside of the cap, whereby a hollow inner space is formed in the mold; and
filling the hollow inner space of the mold with a casting material for producing a cast cap, with the bushing being mounted in the cap.

* * * * *